(12) United States Patent
Winslow

(10) Patent No.: US 9,039,779 B2
(45) Date of Patent: May 26, 2015

(54) ADJUSTABLE LATERAL ARTICULATING CONDYLE

(71) Applicant: Biomet Manufacturing Corp., Warsaw, IN (US)

(72) Inventor: Nathan A. Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 184 days.

(21) Appl. No.: 13/800,740

(22) Filed: Mar. 13, 2013

(65) Prior Publication Data

US 2014/0277525 A1    Sep. 18, 2014

(51) Int. Cl.
*A61F 2/38* (2006.01)
*A61F 2/30* (2006.01)

(52) U.S. Cl.
CPC ..... *A61F 2/3804* (2013.01); *A61F 2002/30542* (2013.01); *A61F 2002/3813* (2013.01); *A61F 2002/30341* (2013.01); *A61F 2002/30604* (2013.01); *A61F 2002/3809* (2013.01)

(58) Field of Classification Search
CPC .................. A61F 2002/3809; A61F 2002/3813
USPC ............................................ 623/20.11–20.13
See application file for complete search history.

(56) References Cited

U.S. PATENT DOCUMENTS

| | | |
|---|---|---|
| 3,547,115 A | 12/1970 | Stevens |
| 3,694,821 A | 10/1972 | Moritz |
| 3,708,805 A | 1/1973 | Scales et al. |
| 3,816,854 A | 6/1974 | Schlein |
| 3,824,630 A | 7/1974 | Johnston |
| 3,852,831 A | 12/1974 | Dee et al. |
| 3,919,725 A | 11/1975 | Swanson et al. |
| 3,939,496 A | 2/1976 | Ling et al. |
| 3,946,445 A | 3/1976 | Bentley et al. |
| 3,990,117 A | 11/1976 | Pritchard et al. |
| 3,991,425 A | 11/1976 | Martin et al. |
| 4,001,603 A | 1/1977 | Wilcox |
| 4,008,495 A | 2/1977 | Cavendish et al. |
| 4,011,603 A | 3/1977 | Steffee |
| 4,038,704 A | 8/1977 | Ring et al. |
| 4,079,469 A | 3/1978 | Wadsworth |

(Continued)

FOREIGN PATENT DOCUMENTS

| | | |
|---|---|---|
| DE | 2806717 | 8/1979 |
| DE | 3417923 A1 | 11/1985 |

(Continued)

OTHER PUBLICATIONS

Computer translation of FR 2 829 688 A1, published on Mar. 21, 2003.*

(Continued)

*Primary Examiner* — David H Willse
(74) *Attorney, Agent, or Firm* — Harness, Dickey

(57) ABSTRACT

An elbow prosthesis is provided and may include a first stem component attached to one of a humerus and an ulna, a second stem component attached to the other of the humerus and the ulna, and a joint disposed between and coupling the first stem component and the second stem component to permit relative movement between the first stem component and the second stem component about a first axis. The elbow prosthesis may additionally include a condyle extending from the joint and including an axis of rotation that is eccentric from the first axis.

24 Claims, 6 Drawing Sheets

(56) References Cited

U.S. PATENT DOCUMENTS

| | | |
|---|---|---|
| 4,129,902 A | 12/1978 | Harmon |
| 4,131,956 A | 1/1979 | Treace |
| 4,131,957 A | 1/1979 | Bokros |
| 4,194,250 A | 3/1980 | Walker |
| 4,206,516 A | 6/1980 | Pilliar |
| 4,224,695 A | 9/1980 | Grundei et al. |
| 4,224,697 A | 9/1980 | Murray et al. |
| 4,242,758 A | 1/1981 | Amis et al. |
| 4,259,752 A | 4/1981 | Taleisnik |
| 4,280,231 A | 7/1981 | Swanson |
| 4,293,963 A | 10/1981 | Gold et al. |
| 4,301,552 A | 11/1981 | London |
| 4,352,212 A | 10/1982 | Greene et al. |
| 4,378,607 A | 4/1983 | Wadsworth |
| 4,383,337 A | 5/1983 | Volz et al. |
| 4,479,271 A | 10/1984 | Bolesky et al. |
| 4,538,306 A | 9/1985 | Dorre et al. |
| 4,659,331 A | 4/1987 | Matthews et al. |
| 4,725,280 A | 2/1988 | Laure |
| 4,759,768 A | 7/1988 | Hermann et al. |
| 4,822,364 A | 4/1989 | Inglis et al. |
| 4,911,719 A | 3/1990 | Merle et al. |
| 4,927,422 A | 5/1990 | Engelhardt |
| 4,936,853 A | 6/1990 | Fabian et al. |
| 5,024,670 A | 6/1991 | Smith et al. |
| 5,030,237 A | 7/1991 | Sorbie et al. |
| 5,207,711 A | 5/1993 | Caspari et al. |
| 5,282,367 A | 2/1994 | Moore et al. |
| 5,282,867 A | 2/1994 | Mikhail |
| 5,314,484 A | 5/1994 | Huene |
| 5,376,121 A | 12/1994 | Huene et al. |
| 5,380,334 A | 1/1995 | Torrie et al. |
| 5,411,555 A | 5/1995 | Nieder |
| 5,507,821 A | 4/1996 | Sennwald et al. |
| 5,507,826 A | 4/1996 | Besselink et al. |
| 5,549,685 A | 8/1996 | Hayes |
| 5,584,835 A | 12/1996 | Greenfield |
| 5,665,087 A | 9/1997 | Huebner |
| 5,702,471 A | 12/1997 | Grundei et al. |
| 5,725,541 A | 3/1998 | Anspach, III et al. |
| 5,725,591 A | 3/1998 | DeCarlo, Jr. et al. |
| 5,782,923 A | 7/1998 | Engelbrecht et al. |
| 5,840,078 A | 11/1998 | Yerys |
| 5,879,395 A | 3/1999 | Tornier et al. |
| 5,980,557 A | 11/1999 | Iserin et al. |
| 6,027,534 A | 2/2000 | Wack et al. |
| 6,120,543 A | 9/2000 | Kubein-Meesenburg et al. |
| 6,162,253 A | 12/2000 | Conzemius et al. |
| 6,290,725 B1 | 9/2001 | Weiss et al. |
| 6,306,171 B1 | 10/2001 | Conzemius |
| 6,379,387 B1 | 4/2002 | Tornier |
| 6,626,906 B1 | 9/2003 | Young |
| 6,656,225 B2 | 12/2003 | Martin |
| 6,699,290 B1 | 3/2004 | Wack et al. |
| 6,767,368 B2 | 7/2004 | Tornier et al. |
| 6,814,757 B2 | 11/2004 | Kopylov et al. |
| 6,890,357 B2 | 5/2005 | Tornier |
| 7,527,650 B2 | 5/2009 | Johnson et al. |
| 2002/0165614 A1 | 11/2002 | Tornier |
| 2004/0186580 A1 | 9/2004 | Steinmann |
| 2004/0243243 A1 | 12/2004 | Tornier |
| 2004/0254574 A1 | 12/2004 | Morrison et al. |
| 2005/0216090 A1 | 9/2005 | O'Driscoll et al. |
| 2006/0173546 A1 | 8/2006 | Berelsman et al. |
| 2006/0247786 A1 | 11/2006 | Ball |
| 2008/0015706 A1 | 1/2008 | Berelsman et al. |
| 2008/0033566 A1 | 2/2008 | Berelsman et al. |
| 2008/0154384 A1 | 6/2008 | Acker et al. |
| 2008/0183291 A1 | 7/2008 | Scheller et al. |
| 2008/0188942 A1 | 8/2008 | Brown et al. |
| 2009/0105839 A1 | 4/2009 | Ikegami et al. |
| 2010/0087928 A1 | 4/2010 | Graham et al. |
| 2010/0179661 A1 | 7/2010 | Berelsman et al. |
| 2010/0222887 A1 | 9/2010 | Katrana et al. |
| 2013/0345818 A1 | 12/2013 | Wagner et al. |

FOREIGN PATENT DOCUMENTS

| | | | |
|---|---|---|---|
| DE | 3940728 A1 | 6/1991 | |
| EP | 1051954 | 11/2000 | |
| EP | 1481653 A1 | 12/2004 | |
| FR | 2419718 A1 | 10/1979 | |
| FR | 2634373 A1 | 1/1990 | |
| FR | 2 829 688 A1 * | 3/2003 | ............... A61F 2/38 |
| GB | 1520162 | 8/1978 | |
| SU | 1560183 A1 | 4/1990 | |
| SU | 1567200 A1 | 5/1990 | |

OTHER PUBLICATIONS

Discovery Elbow System brochure, Surgical Technique, Biomet Orthopedics, Inc., .Copyrgt. 2002 (20 pages total).

Discovery Elbow System, Surgical Technique, Biomet Orthopedics, Inc., Copyright 2008, 28 pages.

Final Office Action for U.S. Appl. No. 11/384,943 Mailed Dec. 12, 2011.

Final Office Action for U.S. Appl. No. 11/384,943, mailed Oct. 27, 2010.

International Preliminary Report on Patentability and Written Opinion for PCT/US2009/057449 Mailed Sep. 9, 2011.

International Search Report and Written Opinion for PCT/US2009/057449 mailed Feb. 21, 2011.

International Search Report and Written Opinion for PCT/US2010/049314 mailed Feb. 21, 2011.

International Search Report and Written Opinion of the International Searching Authority regarding International Application No. PCT/US2012/045207, mailed Nov. 8, 2012.

International Search Report for PCT/US01/22338 mailed Jan. 3, 2002 based on U.S. Appl. No. 60/219,103, filed Jul. 18, 2000.

Joint Replacement, Surgery, .Copyrgt. DePuy Orthopedics, Inc., www.jointreplacement.com/xq/ASP.default/mn.local/pg.list/joint.sub.--id.2- /list.sub.--id.59/newFont.2/joint.sub.--nm.Elbow/local.sub.--id.18/qx/defa- ult.htm, 2000-2004.

Joint Replacement, Surgery, .Copyrgt. DePuy Orthopaedics, Inc., www.jointreplacement.com/xq/ASP.default/mn.local/pg.list/joint.sub.--id.2- /list.sub.--id.59/newFont.2/joint.sub.--nm.Elbow/local.sub.--id.18/qx/defa- ult.htm, 2000-2005.

Non-Final Office Action for U.S. Appl. No. 12/391,904, mailed Nov. 1, 2012.

Non-Final Office Action for U.S. Appl. No. 11/384,943, mailed Apr. 12, 2011.

Non-Final Office Action for U.S. Appl. No. 11/384,943, mailed Apr. 13, 2010.

Non-Final Office Action regarding U.S. Appl. No. 12/562,616, mailed May 17, 2012.

Non-Final Office Action regarding U.S. Appl. No. 12/780,424, mailed Nov. 2, 2012.

Sorbie-Questor.RTM. Total Elbow System, Extremities (2003) Wright Medical Technology, Inc., 1 page.

International Search Report and Written Opinion of the International Searching Authority regarding International Application No. PCT/US2014/021970, mailed May 12, 2014.

* cited by examiner

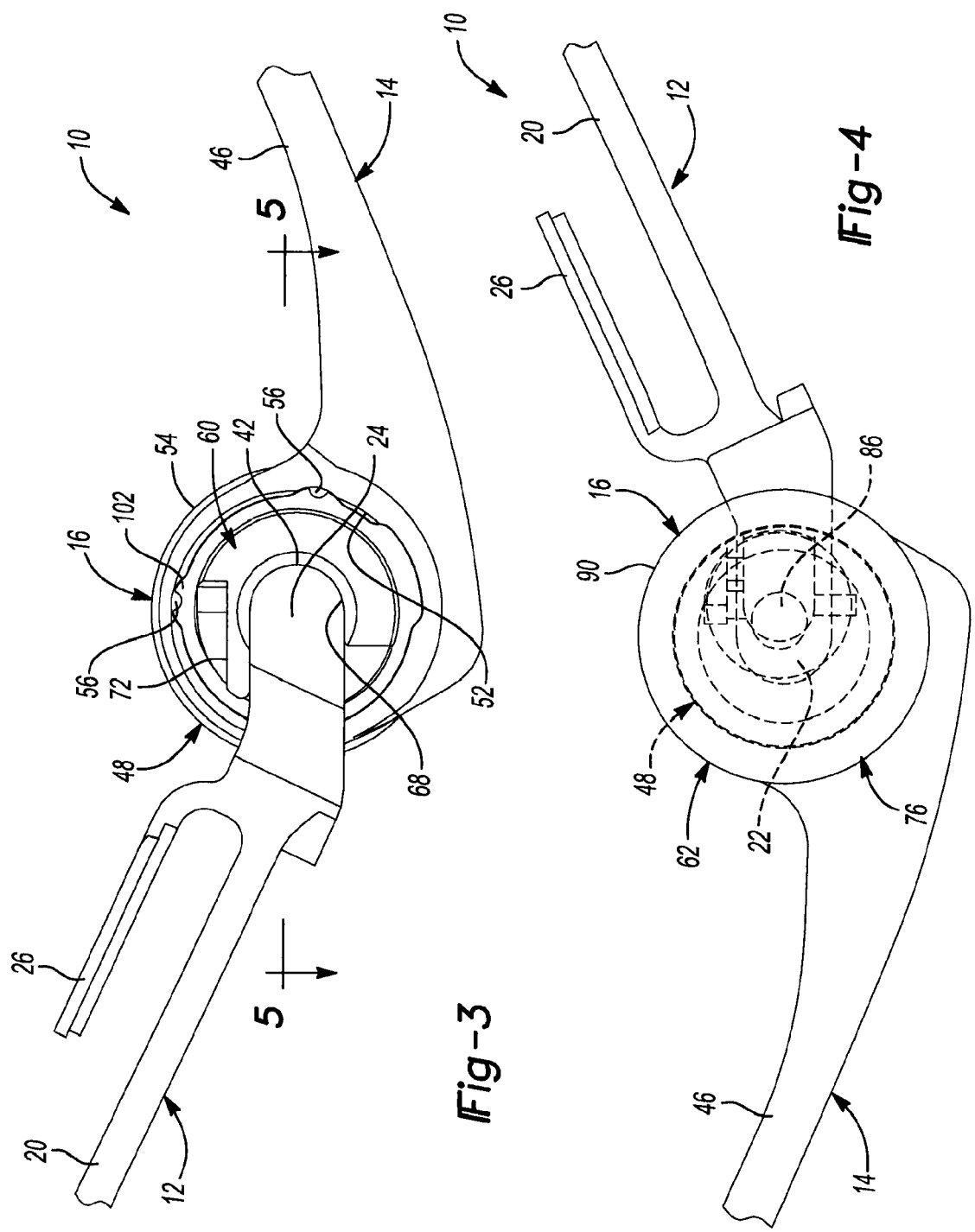

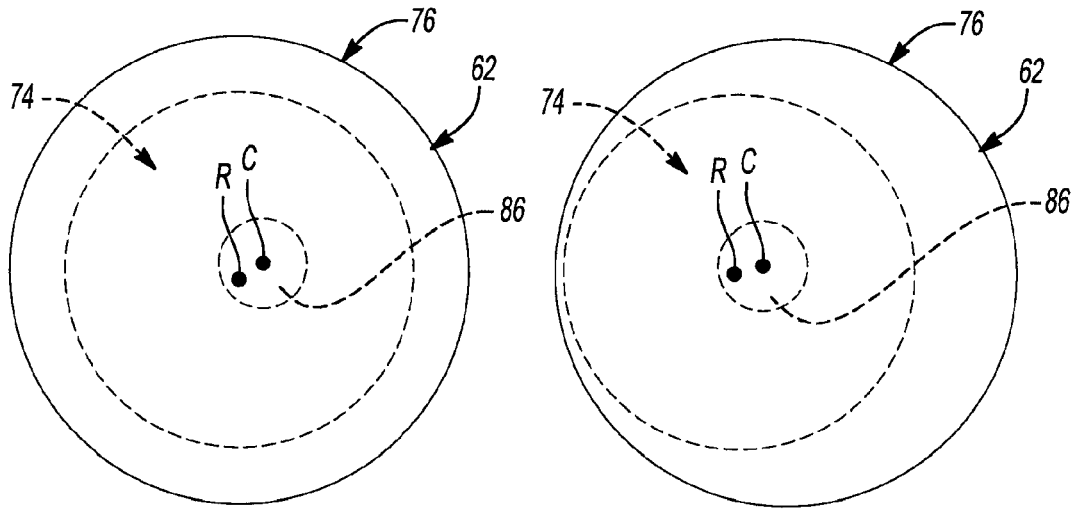
Fig-7    Fig-8
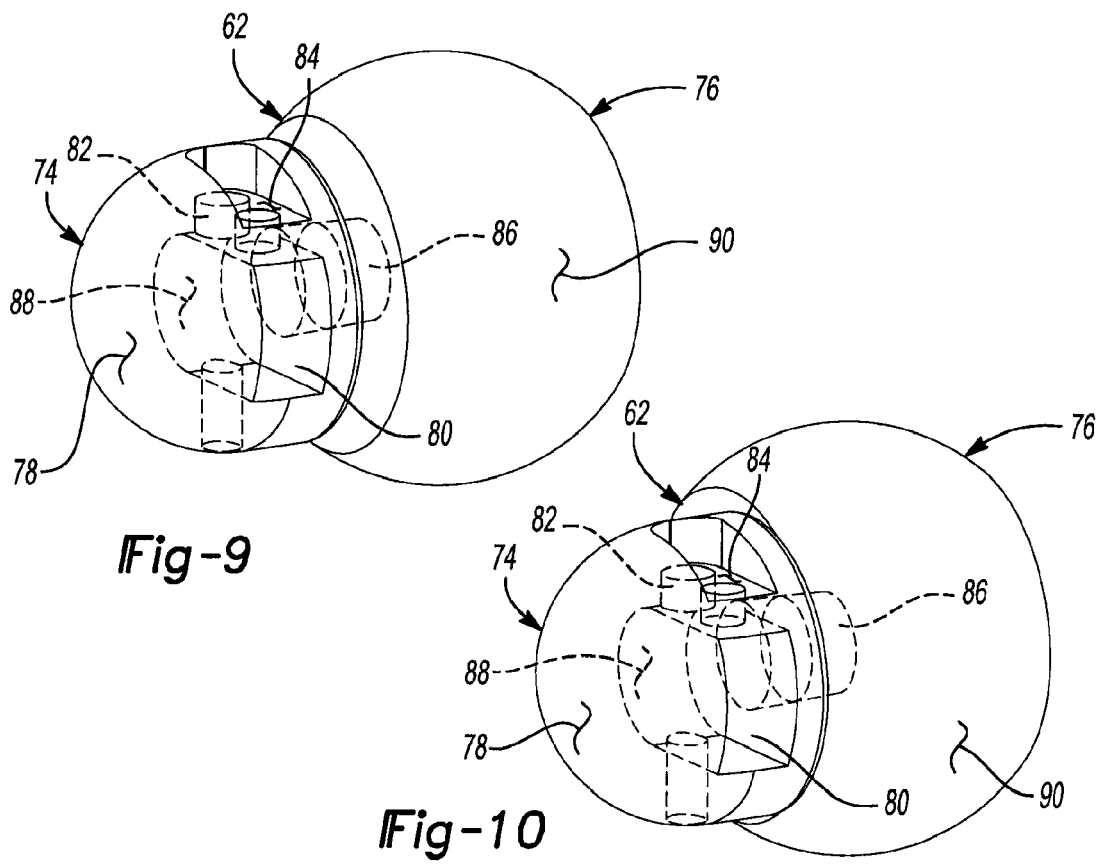
Fig-9
Fig-10

ADJUSTABLE LATERAL ARTICULATING CONDYLE

FIELD

The present disclosure relates to an elbow prosthesis and more particularly to an elbow prosthesis incorporating an articulating condyle.

BACKGROUND

This section provides background information related to the present disclosure which is not necessarily prior art.

Elbow prostheses provide articulation between the proximal radius and the distal humerus following total elbow arthroplasty. One such elbow prosthesis is a linked or constrained elbow prosthesis that includes a first component attached to the humerus and a second component attached to the ulna. A joint or hinge disposed at a junction of the first component and the second component permits relative movement between the first component and the second component and, thus, permits movement between the humerus and the ulna at the proximal radius and the distal humerus.

Conventional elbow prostheses sometimes include a pair of condyle components extending from the medial and lateral sides of the joint, respectively. The condyle components are designed to approximate the function of the lateral epicondyle and the medial epicondyle and are intended to provide increased articular surface contact at the proximal radius and the distal humerus once the prosthesis is installed in the humerus and the ulna.

In total elbow arthroplasty, the anatomic articulation between the radius and humerus is preserved, if possible. In cases where this is not possible, articulation between the radius and humerus must be replaced with a prosthesis. While conventional elbow prostheses adequately provide articulation between the proximal ulna and the distal humerus, conventional radio-humeral elbow prostheses are not adjustable and therefore cannot be adjusted to different boney anatomies, different states of joint laxity, and different qualities and states of soft tissue tension. For example, conventional condyle components cannot be adjusted during surgery to accommodate the exact distance between the head of the proximal radius and the condyle component, which causes difficulty in tensioning the condyle component with the proximal end of the radius. Such difficulty results in the need for multiple elbow prostheses having different sized condyle components. The different sized condyle components allow a surgeon to ensure proper articulation and support of the elbow prosthesis once installed but add to the overall cost and complexity of the procedure.

SUMMARY

This section provides a general summary of the disclosure, and is not a comprehensive disclosure of its full scope or all of its features.

An elbow prosthesis is provided and may include a first stem component attached to one of a humerus and an ulna, a second stem component attached to the other of the humerus and the ulna, and a joint disposed between and coupling the first stem component and the second stem component to permit relative movement between the first stem component and the second stem component about a first axis. The elbow prosthesis may additionally include a condyle extending from the joint and including an axis of rotation that is eccentric from the first axis.

In another configuration, an elbow prosthesis is provided and may include a first stem component attached to one of a humerus and an ulna, a second stem component attached to the other of the humerus and the ulna, and a joint disposed between and coupling the first stem component and the second stem component to permit relative movement between the first stem component and the second stem component about a first axis. The elbow prosthesis may additionally include a first condyle component rotatable with one of the first stem component and the second stem component about the first axis and a second condyle component rotatable relative to the first condyle component about a second axis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a partial side view of the elbow prosthesis of FIG. 1;

FIG. 4 is a partial side view of the elbow prosthesis of FIG. 1;

FIG. 7 is a side view of the elbow prosthesis of FIG. 5 showing the lateral condyle in the neutral state;

FIG. 8 is a side view of the elbow prosthesis of FIG. 6 showing the lateral condyle in the articulated state;

FIG. 9 is a perspective view of a condyle assembly of the elbow prosthesis of FIG. 1 in a neutral state;

FIG. 10 is a perspective view of a condyle assembly of the elbow prosthesis of FIG. 1 in an articulated state;

Corresponding reference numerals indicate corresponding parts throughout the several views of the drawings.

DETAILED DESCRIPTION

Figure 1:
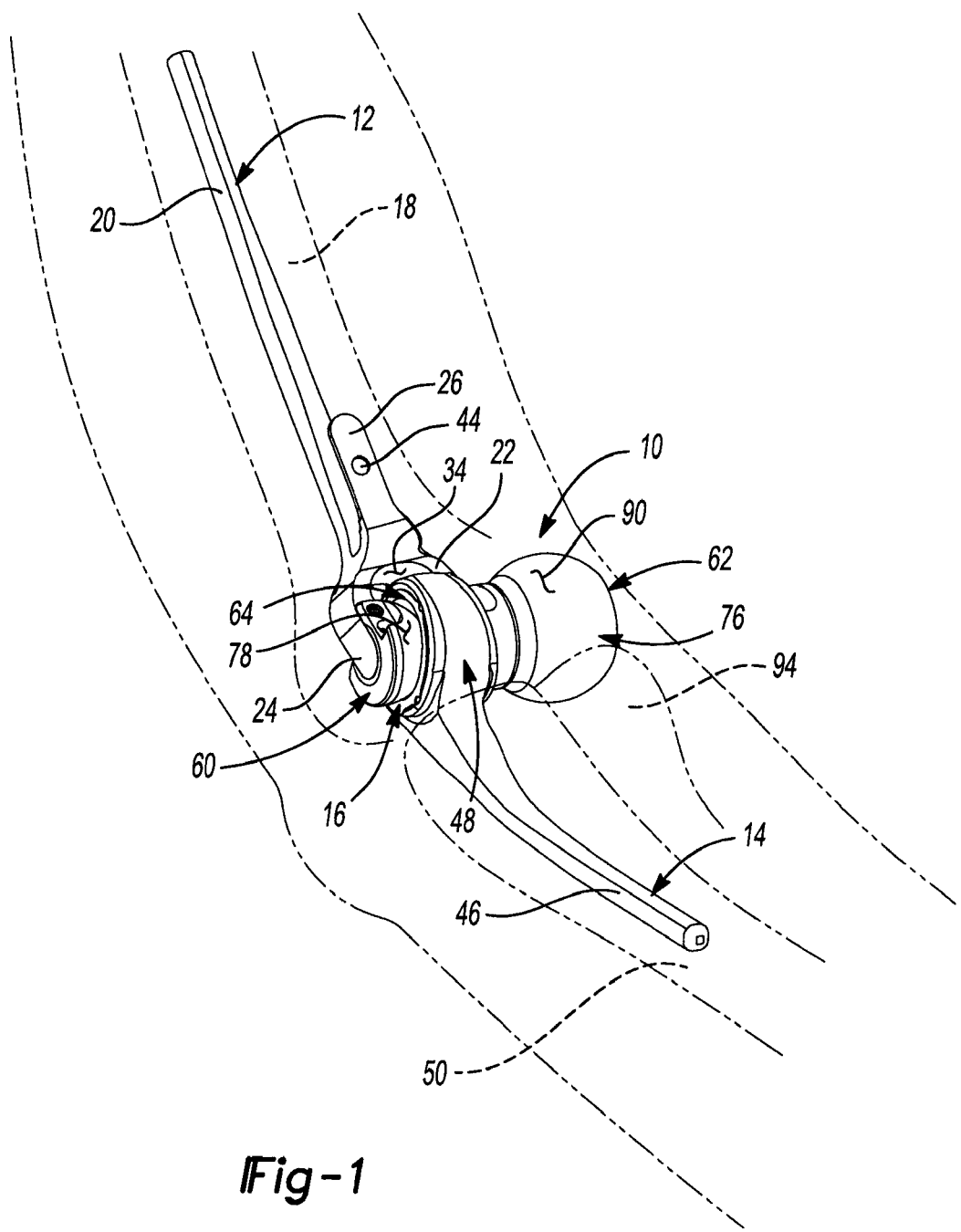
FIG. 1 is a perspective view of an elbow prosthesis in accordance with the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to the figures, an elbow prosthesis 10 is provided and may include a first stem component 12, a second stem component 14, and a hinge assembly 16 disposed generally between the first stem component 12 and the second stem component 14. The hinge assembly 16 may join the first stem component 12 and the second stem component 14 and may facilitate relative movement between the first stem component 12 and the second stem component 14.

The first stem component 12 may be received within a cavity (not shown) formed in a distal humerus 18 (FIG. 1) and may include an elongate, tapered body 20, a first arm 22, a second arm 24, and a hook portion 26. The tapered body 20 may extend in an opposite direction than the first arm 22 and the second arm 24 and may be received within a channel formed in the humerus 18. The tapered body 20 may be secured within the channel formed in the humerus 18 by applying a force to the body 20 along a longitudinal axis thereof.

Applying a force to the body 20 in the foregoing manner causes the body 20 to be secured within the humerus 18 via a friction fit. Namely, the channel formed in the humerus 18 may include a female taper that decreases in size in a direction extending from the distal humerus to the proximal humerus. The female taper formed in the channel of the humerus 18 may cooperate with the male taper of the tapered body 20 to allow the tapered body 20 to frictionally engage the female taper of the humerus 18, thereby fixing the body 20 within and relative to the humerus 18. Bone cement and/or other suitable adhesives may also be used to secure the body 20 within the humerus 18.

The first arm 22 and the second arm 24 may extend in an opposite direction than the tapered body 20 and may cooperate to provide the first stem component 12 with a substantially U-shaped channel 28. Specifically, the U-shaped channel 28 may be formed by a side surface 30 of the first arm 22, a side surface 32 of the second arm 24, and an arcuate surface 34 that extends generally between and connects the side surfaces 30, 32.

The first arm 22 may include a bore 36 and a distal end surface 38. Likewise, the second arm 24 may include a bore 40 and a distal end surface 42. The bores 36, 40 of the first arm 22 and the second arm 24, respectively, may cooperate with the hinge assembly 16 to position and retain the hinge assembly 16 between the side surface 30 of the first arm 22 and the side surface 32 of the second arm 24, as will be described in greater detail below.

The hook portion 26 may extend from a junction of the tapered body 20 and the first and second arms 22, 24. Further, the hook portion 26 may be spaced apart and separated from the tapered body 20 and may include an attachment aperture 44. Spacing the hook portion 26 from the tapered body 20 may permit a portion of the humerus 18 to be received generally between the tapered body 20 and the hook portion 26. As such, the hook portion 26 may oppose a portion of the humerus 18, which may permit a fastener (not shown) to be received through the attachment aperture 44 to secure the hook portion 26 and, thus, the first stem component 12, to the humerus 18. As with the tapered body 20, a suitable bone cement and/or adhesive may be used in conjunction with the hook portion 26 and the humerus 18 to secure the hook portion 26 to the humerus 18.

The second stem component 14 may be joined to the first stem component 12 via the hinge assembly 16 and may include an elongate, tapered body 46 and an attachment feature 48. The tapered body 46 may be received within a channel (not shown) formed in the ulna 50 (FIG. 1). The channel formed in the ulna 50 may include a female taper such that when the male taper of the body 46 is inserted into the channel and a force is applied along a longitudinal axis of the body 46, the male taper of the body 46 engages the female taper of the channel, thereby joining the body 46 to the ulna 50 via a friction fit. The tapered body 46 may further be attached to the channel of the ulna 50 via a suitable bone cement and/or other adhesive.

The attachment feature 48 may be formed at one end of the second stem component 14 and may include a bore 52 and an outer, arcuate surface 54. The bore 52 may include a series of retention features 56 that cooperate with the hinge assembly 16 to retain a portion of the hinge assembly 16 within the attachment feature 48. Finally, the attachment feature 48 may include an attachment aperture 58 that is formed through a wall of the attachment feature 48 and extends generally between the arcuate surface 54 and the bore 52. As such, the attachment aperture 58 may provide communication with the bore 52 from an area outside the attachment feature 48. In one configuration, the attachment aperture 58 may receive a fastener (not shown) to secure a portion of the hinge assembly 16 within the attachment feature 48, as will be described in greater detail below.

The hinge assembly 16 may be disposed at a junction of the first stem component 12 and the second stem component 14 and may include a first condyle 60, a second condyle 62, and a bearing member 64. The first condyle 60 may include an articulating surface 66, a channel 68, and a bore 70 formed in a substantially flat surface 72. The articulating surface 66 may provide the first condyle 60 with a substantially hemispherical shape that is matingly received by the bearing member 64 to allow the first condyle 60 to articulate within and relative to the bearing member 64 about the articulating surface 66.

The channel 68 may be formed on an opposite side of the first condyle 60 from the articulating surface 66 and may include a shape that matingly receives the distal end surface 42 of the second arm 24. Providing the channel 68 with the same shape as the distal end surface 42 of the second arm 24 allows the second arm 24 to be properly positioned relative to and within the channel 68 when the second arm 24 is received by the first condyle 60.

Once the second arm 24 is received by the channel 68 of the first condyle 60 such that the distal end surface 42 is fully seated within the channel 68, the bore 70 of the first condyle 60 may be aligned with the bore 40 of the second arm 24. Alignment between the bore 40 formed in the second arm 24 and the bore 70 formed in the first condyle 60 allows a fastener (not shown) to be inserted into and through the bores 40, 70 to fix the first condyle 60 for movement with the second arm 24.

The second condyle 62 may include a medial component 74 and a lateral component 76. The terms "medial" and "lateral" are used to describe components 74 and 76 relative to a bone axis and are not necessarily "medial" and "lateral" to the body. The medial component 74 may include an articulating surface 78, a pocket 80, and a bore 82 formed in a substantially flat surface 84. The medial component 74 may additionally include a projection 86 extending from an opposite side of the medial component 74 than the articulating surface 78.

Figure 5:
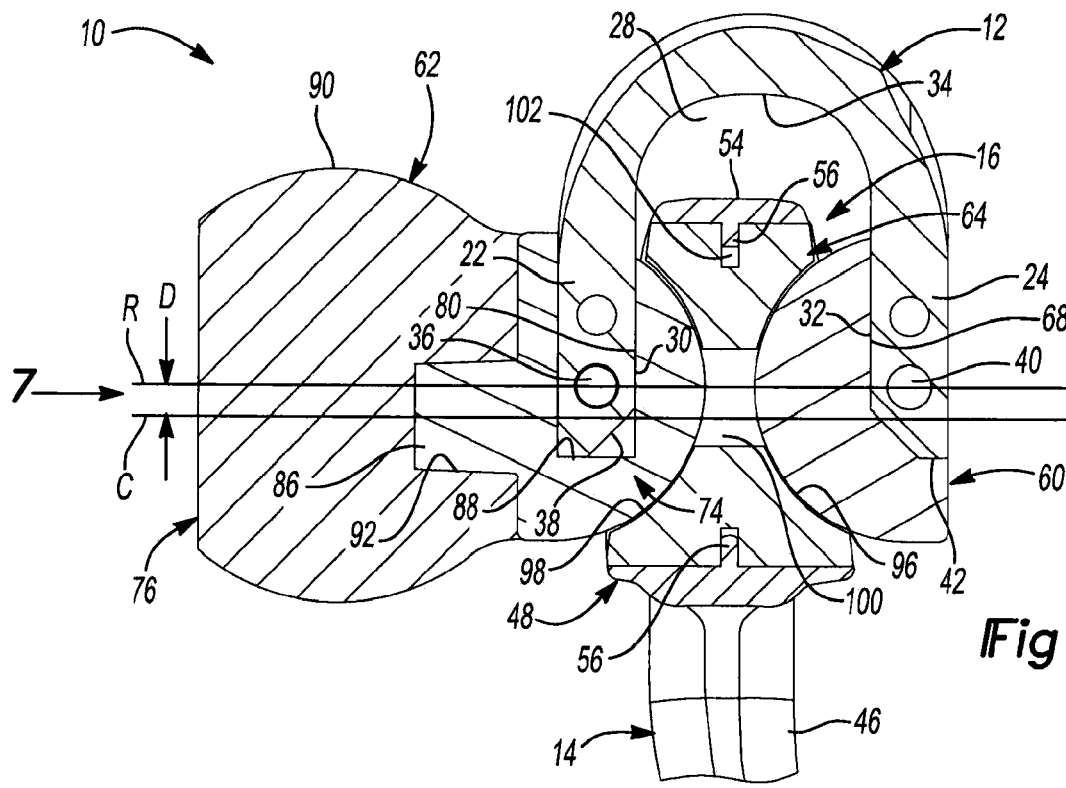
FIG. 5 is a partial cross-sectional view of the elbow prosthesis of FIG. 1 taken along line 5-5 of FIG. 3.
Figure 6:
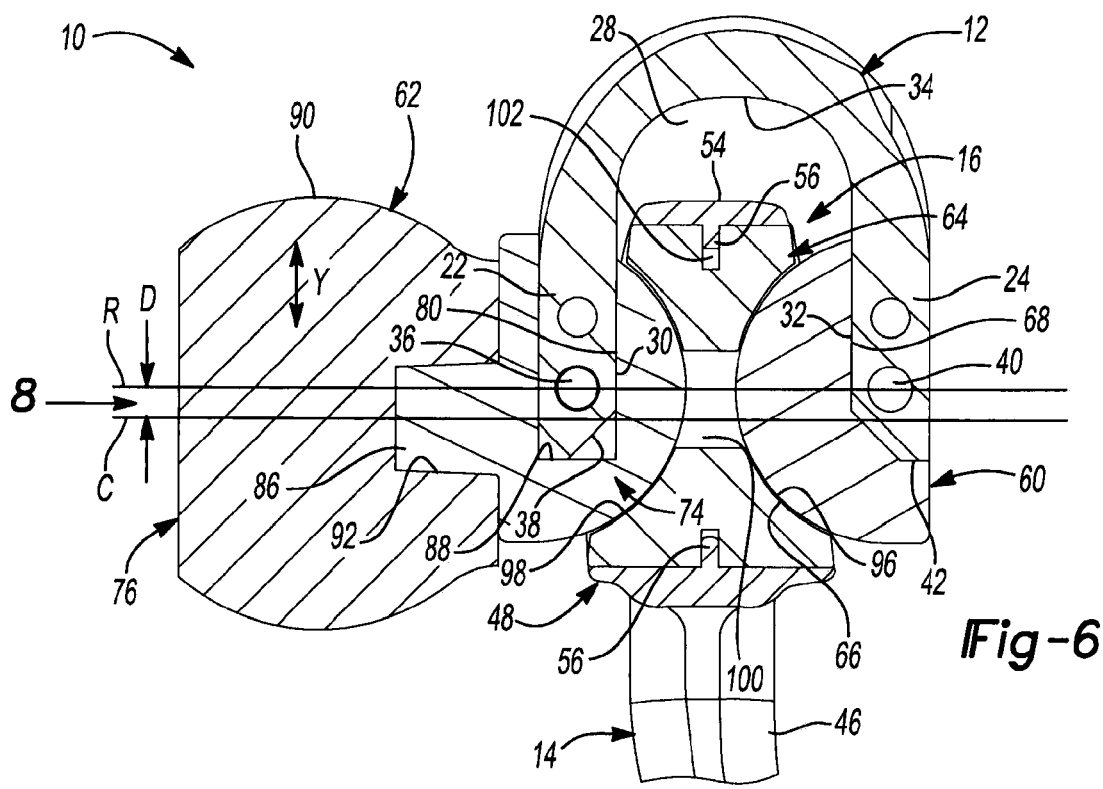
FIG. 6 is a partial cross-sectional view of the elbow prosthesis of FIG. 1 showing a lateral condyle in an articulated state.

The articulating surface 78 may be rotatably attached to the bearing member 64 to rotatably support the medial component 74 relative to the bearing member 64. The pocket 80 may be formed into the articulating surface 78 (FIGS. 9 and 10) and may receive the first arm 22 therein. Specifically, the first arm 22 may be inserted into the pocket 80 until the distal end surface 38 of the first arm 22 contacts an end surface 88 of the pocket (FIGS. 5 and 6). At this point, the first arm 22 is fully inserted into the pocket 80 such that the bore 82 of the second condyle 62 is aligned with the bore 36 of the first arm 22. As with the first condyle 60, alignment between the bore 36 of the first arm 22 and the bore 82 of the second condyle 62 allows a fastener (not shown) to be inserted into and through the bores 36, 82 to fix the medial component 74 for movement with the first arm 22.

The projection 86 may extend from the medial component 74 and may be offset from an axis of rotation (R) of the medial component 74. Specifically, a central axis (C) extending through a center of the projection 86 may be offset from the axis of rotation (R) of the medial component 74 by a distance (D), as shown in FIGS. 5 and 6. In short, the projection 86 may be eccentric from the axis of rotation (R) of the medial component 74.

The lateral component 76 may be rotatably attached to the medial component 74 and may include an engagement surface 90 and a blind bore 92 formed on an opposite side of the lateral component 76 than the engagement surface 90. The blind bore 92 may include a female taper that receives the projection 86 of the medial component 74. Specifically, the projection 86 may include a male taper that rotatably receives the female taper of the blind bore 92 to rotatably attach the lateral component 76 to the medial component 74.

The blind bore 92 may be formed in the lateral component 76 such that the blind bore 92 is eccentric from a central axis of the lateral component 76 (axis of rotation (R) in FIG. 5) in a similar fashion as the projection 86 is eccentric to the axis of rotation (R) of the medial component 74. For example, the blind bore 92 may include a central axis that is concentric with the central axis (C) of the projection 86. The central axis of the blind bore 92 may be offset relative to the central axis of the lateral component 76 by the distance (D), as represented in FIGS. 5 and 7 (FIGS. 5 and 7 show the central axis of the lateral component 76 as being concentric with the axis of rotation (R) of the medial component 74 when the lateral component 76 is in the neutral state).

Because the blind bore 92 is eccentric from the central axis of the lateral component 76 and, further, because the projection 86 is eccentric from an axis of rotation of the medial component 74, rotation of the lateral component 76 relative to the medial component 74 about the projection 86 causes the lateral component 76 to move from a neutral state (FIG. 5) to an articulated state (FIG. 6). As shown in FIG. 5, the offset of the blind bore 92 from the central axis of the lateral component 76 and the offset of the projection 86 from the axis of rotation of the medial component 74 are equal, which allows the lateral component 76 to be positioned in neutral state. Rotation of the lateral component 76 about the projection 86 results in a net offset (i.e., in the plane of FIG. 6) of the lateral component 76 in the direction (Y). Such adjustment of the lateral component 76 relative to the medial component 74 allows the engagement surface 90 of the lateral component 76 to be properly positioned relative to the head of the proximal radius 94 (FIG. 1) when the elbow prosthesis 10 is installed by a surgeon.

The bearing member 64 may be received by the attachment feature 48 and may include a first bearing surface 96, a second bearing surface 98, a central bore 100, and a series of retention features 102. The bearing member 64 may be positioned within and received by the bore 52 of the attachment feature 48 such that the retention features 102 cooperate with the retention features 56 to retain and position the bearing member 64 within the bore 52. Once the bearing member 64 is properly positioned relative to and within the bore 52 of the attachment feature 48, a fastener (not shown) may be received through the attachment aperture 58 and may engage the bearing member 64 to retain the bearing member 64 in a desired position within the bore 52.

The first bearing surface 96 may oppose the first condyle 60 such that the articulating surface 66 is in contact with the first bearing surface 96. Accordingly, when the first condyle 60 is moved with the second arm 24 of the first stem component 12 relative to the second stem component 14, the articulating surface 66 moves relative to and is in engagement with the first bearing surface 96 of the bearing member 64. Likewise, the second bearing surface 98 may oppose and receive the second condyle 62 such that the articulating surface 78 of the medial component 74 engages and is in contact with the second bearing surface 98. Accordingly, when the medial component 74 moves with the first arm 22 of the first stem component 12 relative to the second stem component 14, the articulating surface 78 moves relative to and is engagement with the second bearing surface 98.

Figure 2:
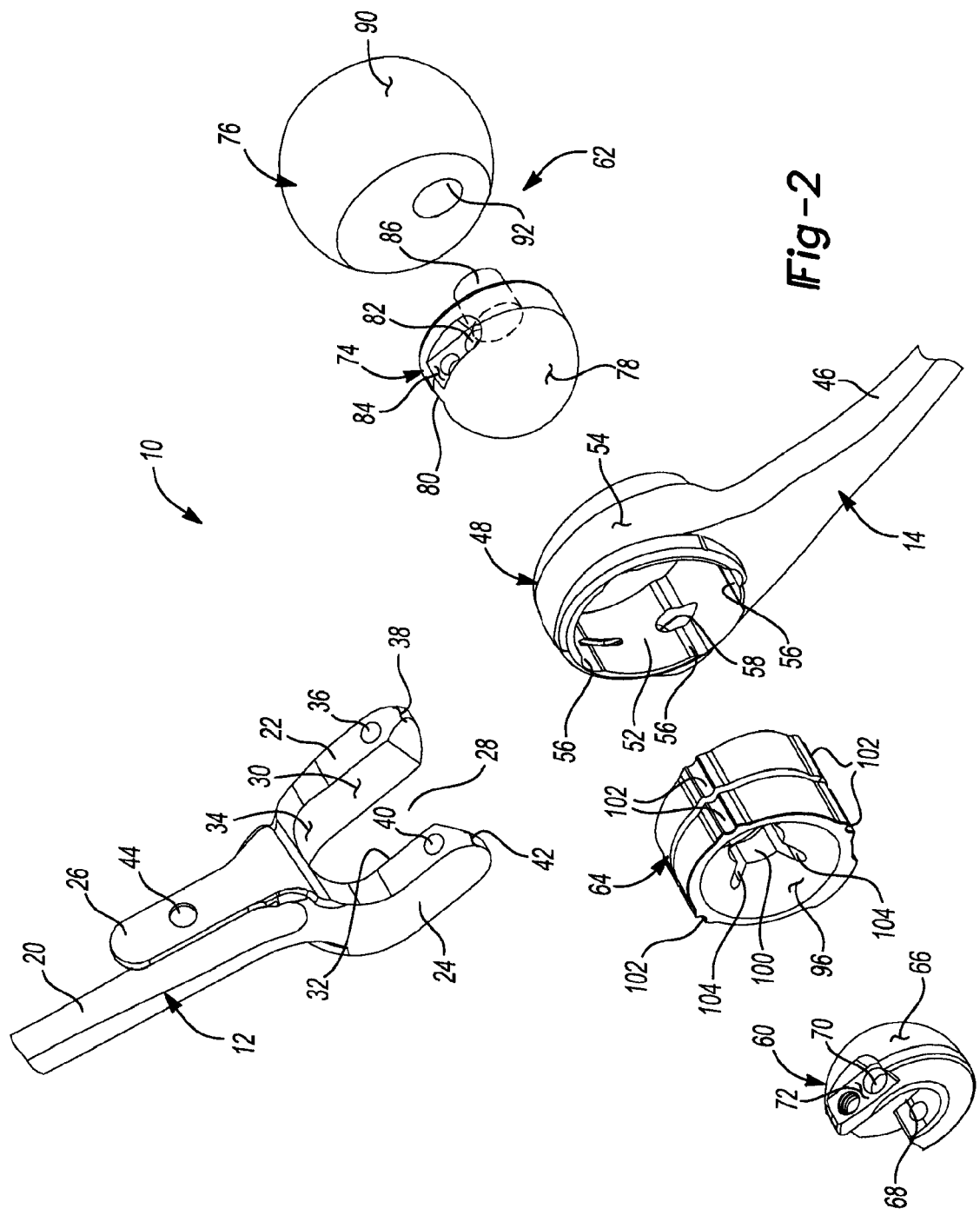
FIG. 2 is an exploded view of the elbow prosthesis of FIG. 1.

The central bore 100 may extend between the first bearing surface 96 and the second bearing surface 98 and may include a series of extensions 104 (FIG. 2) that are formed into the bearing member 64. The extensions 104 may radiate from the central bore 100 and may extend into the first bearing surface 96 and the second bearing surface 98. The extensions 104 may cooperate with the central bore 100 to provide the bearing member 64 with a degree of flexibility at the first bearing surface 96 and the second bearing surface 98 proximate to the central bore 100. The flexibility provided by the central bore 100 and the extensions 104 allows the first bearing surface 96 and the second bearing surface 98 to flex during movement of the first condyle 60 and the second condyle 62 relative to the bearing member 64 during relative movement between the first stem component 12 and the second stem component 14.

With continued reference to the figures, installation of the elbow prosthesis 10 during a total elbow arthroplasty procedure will be described in detail.

The first stem component 12 may be received by a channel formed in the humerus 18 and the second stem component 14 may be received in a channel formed in the ulna 50, as described above. The hinge assembly 16 may be assembled to the first stem component 12 and to the second stem component 14 to permit relative movement between the first stem component 12 and the second stem component 14. The hinge assembly 16 may be assembled to the first stem component 12 and to the second stem component 14 prior to installation of the first stem component 12 into the humerus 18 and prior to installation of the second stem component 14 into the ulna 50. Nonetheless, attachment of the hinge assembly 16 to the first stem component 12 and to the second stem component 14 will be described hereinafter following installation of the first stem component 12 into the humerus 18 and following installation of the second stem component 14 into the ulna 50.

A surgeon may initially create an incision proximate to an elbow joint of a patient to gain access to the distal end of the humerus 18, the proximal end of the ulna 50, and the head of the proximal radius 94. Once access to the humerus 18, the ulna 50, and the radius 94 is accomplished, the humerus 18 may be prepared by forming a channel therein. The channel formed into the humerus 18 may include a female taper that receives the male tapered body 20 of the first stem component 12. A force may be applied to the tapered body 20 of the first stem component 12 to insert the first stem component 12 into the channel of the humerus 18, thereby creating a friction fit between the tapered body 20 of the first stem component 12 and the channel. Bone cement and/or a suitable adhesive may also be used to secure the first stem component 12 within the humerus 18.

The second stem component 14 may be inserted into a channel formed in the ulna 50 in a similar fashion as described above with respect to the first stem component 12. Namely, a channel having a female taper may be formed in the ulna 50 and may receive the male tapered body 46 of the second stem component 14. A force may be applied in a direction substantially along a longitudinal axis of the second stem component 14 to drive the second stem component 14 into the channel formed in the ulna 50.

Urging the male tapered body 46 of the second stem component 14 into the channel formed in the ulna 50 creates a friction fit between the tapered body 46 of the second stem component 14 and the channel formed in the ulna 50. The friction fit fixes the second stem component 14 for movement with the ulna 50. Bone cement and/or a suitable adhesive may also be used to secure the second stem component 14 within the ulna 50. Once the first stem component 12 is attached to the humerus 18 and the second stem component 14 is attached to the ulna 50, the hinge assembly 16 may be attached to the first stem component 12 and the second stem component 14.

The bearing member 64 of the hinge assembly 16 may initially be positioned relative to the second stem component 14 such that the bearing member 64 opposes the bore 52 formed in the attachment feature 48. The bearing member 64 may be properly aligned relative to the attachment feature 48 by aligning the retention features 102 of the bearing member 64 relative to the retention features 56 of the bore 52. Once the retention features 102 of the bearing member 64 are properly aligned with the retention features 56 of the bore 52, the bearing member 64 may be moved into the attachment feature 48 of the second stem component 14.

Once the bearing member 64 is moved into a desired location relative to and within the bore 52 of the attachment feature 48, a fastener (not shown) may be inserted into the attachment aperture 58 of the attachment feature 48 and may engage the bearing member 64 to fix a position of the bearing member 64 relative to and within the bore 52 of the attachment feature 48. At this point, the bearing member 64 is fixed relative to the second stem component 14 and is restricted from being removed from the bore 52 by the fastener received through the attachment aperture 58 and is restricted from rotating within the bore 52 due to engagement between the retention features 102 of the bearing member 64 and the retention features 56 of the bore 52.

The first condyle 60 may be attached to the second arm 24 of the first stem component 12 by inserting the second arm 24 into the channel 68. The second arm 24 may be advanced into the channel 68 until the distal end surface 42 of the second arm 24 abuts a distal end of the channel 68. At this point, the bore 40 formed through the second arm 24 may be aligned with the bore 70 formed through the first condyle 60. A fastener (not shown) may be inserted through the bore 70 of the first condyle 60 and may be inserted through the bore 40 formed in the second arm 24 to fix the first condyle 60 for movement with the second arm 24 of the first stem component 12.

The first condyle 60 may be positioned relative to and received by the first bearing surface 96 of the bearing member 64 such that the articulating surface 66 of the first condyle 60 opposes and is in contact with the first bearing surface 96 of the bearing member 64. Accordingly, when the first stem component 12 is moved relative to the second stem component 14, the articulating surface 66 may be in contact with and may bear against the first bearing surface 96 of the bearing member 64.

The second condyle 62 may be attached to the first arm 22 of the first stem component 12 by inserting the first arm 22 into the pocket 80 formed in the medial component 74. The first arm 22 may be advanced into the pocket 80 until the distal end surface 38 of the first arm 22 contacts the end surface 88 of the pocket 80. At this point, the bore 36 formed through the first arm 22 may be aligned with the bore 82 of the medial component 74. A fastener (not shown) may be received through the bore 82 of the medial component 74 and may be received through the bore 36 of the first arm 22 such that the medial component 74 is fixed for movement with the first stem component 12. Accordingly, when the first stem component 12 is moved relative to the second stem component 14, the medial component 74 is likewise moved relative to the second stem component 14.

The medial component 74 may be positioned relative to and may be received by the second bearing surface 98 of the bearing member 64. Specifically, the articulating surface 78 of the medial component 74 may be received by and may be in contact with the second bearing surface 98 such that when the medial component 74 is moved relative to the second stem component 14, the articulating surface 78 of the medial component 74 is in contact with and bears against the second bearing surface 98 of the bearing member 64.

The lateral component 76 may be attached to the medial component 74 by aligning the blind bore 92 of the lateral component 76 with the projection 86 of the medial component 74. A force may be applied to the lateral component 76 to cause the projection 86 of the medial component 74 to be received within the blind bore 92. When the lateral component 76 is initially installed on the medial component 74, the lateral component 76 may be in a neutral state (FIG. 7) such that the axis of rotation (R) of the medial component 74 is aligned with the central axis of the lateral component 76.

At this point, a force may be applied to the lateral component 76 to cause the lateral component 76 to rotate relative to the medial component 74 about the projection 86. Because the center (C) of the projection 86 is offset from the axis of rotation (R) of the medial component 74 and, further, because a center of the blind bore 92 is offset from the central axis of the lateral component 76, rotation of the lateral component 76 about the projection 86 causes the lateral component 76 to articulate and move relative to the medial component 74 in a linear direction.

For example, rotation of the lateral component 76 about the projection 86 may result in a net offset (i.e., in the plane of FIG. 6) of the lateral component 76 in the direction (Y). Such movement may be performed by the surgeon when installing the elbow prosthesis 10 to allow the lateral component 76 of the second condyle 62 to be properly tensioned and in contact with the head of the proximal radius 94. Once a desired position of the lateral component 76 is achieved such that the engagement surface 90 of the lateral component 76 is in engagement with the head of the proximal radius 94, a force may be applied to the lateral component 76 to fully insert the projection 86 into the blind bore 92 of the lateral component 76.

As described above, the projection 86 may include a male taper and the blind bore 92 may include a female taper. Accordingly, when the projection 86 is driven into the blind bore 92, engagement between the male taper of the projection 86 and the female taper of the blind bore 92 fixes a rotational position of the lateral component 76 relative to the medial component 74 and prevents further movement of the lateral component 76 relative to the medial component 74.

Once the lateral component 76 is installed on the medial component 74 and the projection 86 is fully seated within the blind bore 92 such that a rotational position of the lateral component 76 is fixed relative to the medial component 74, the surgeon may apply a force to one or both of the first stem component 12 and the second stem component 14 to ensure that the hinge assembly 16 provides a desired range of motion. Applying a force to one or both of the first stem component 12 and the second stem component 14 causes the first condyle 60 to move relative to the bearing member 64 and causes the second condyle 62 to move relative to the bearing member 64. Specifically, the articulating surface 66 of the first condyle 60 engages and moves relative to the first bearing surface 96 of the bearing member 64. Likewise, the articulating surface 78 of the medial component 74 engages and moves relative to the second bearing surface 98 of the bearing member 64.

The foregoing movement likewise causes the engagement surface 90 of the lateral component 76 to engage and move relative to the head of the proximal radius 94. Engagement between the engagement surface 90 of the lateral component 76 and the head of the proximal radius 94 provides stability to the medial component 74 and enhances articulation of the lateral component 76 with the head of the proximal radius 94.

Providing the lateral component 76 with a degree of adjustment relative to the medial component 74 allows the surgeon to adjust the position of the lateral component 76 relative to the head of the proximal radius 94 during surgery and, therefore, ensures that the lateral component 76 will adequately support and articulate relative to the head of the proximal radius 94 during use of the elbow prosthesis 10 and through the range of motion.

Figure 11:
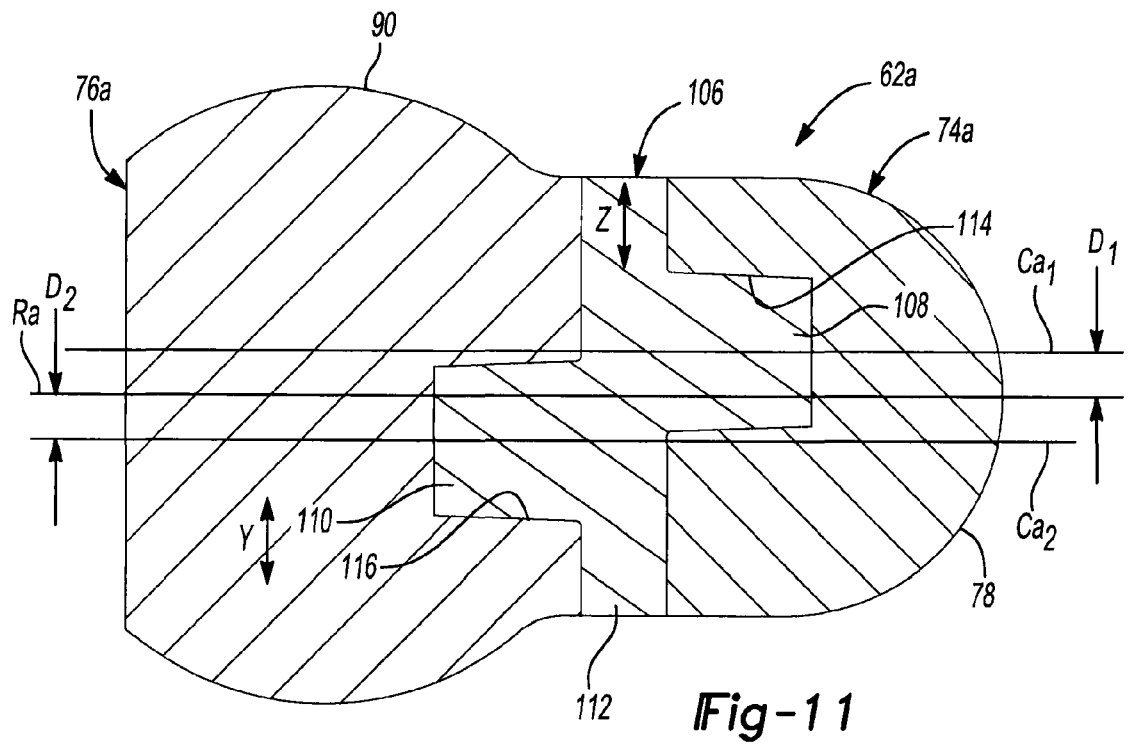
FIG. 11 is a cross-sectional view of an alternate condyle assembly for use in conjunction with the elbow prosthesis of FIG. 1.

With particular reference to FIG. 11, a second condyle 62a is provided for use with the elbow prosthesis 10. The second condyle 62a replaces the second condyle 62 and may include a medial component 74a, a lateral component 76a, and an intermediate component 106 disposed generally between the medial component 74a and the lateral component 76a.

In view of the substantial similarity in structure and function of the components associated with the second condyle 62 with respect to the second condyle 62a, like reference numerals are used hereinafter and in the drawings to identify like components while like reference numerals containing letter extensions are used to identify those components that have been modified.

The intermediate component may include a first projection 108, a second projection 110, and a main body 112 disposed between the first projection 108 and the second projection 110. The first projection 108 may include a male taper and may be received within a blind bore 114 formed in the medial component 74a. The blind bore 114 may include a female taper and may matingly receive the male taper of the first projection 108.

The first projection 108 may be offset from an axis of rotation (Ra) of the medial component 74a. As such, a central axis ($Ca_1$) of the first projection 108 may be spaced apart and separated from the axis of rotation (Ra) of the medial component 74a by a distance ($D_1$). Because the central axis ($Ca_1$) of the first projection 108 may be offset from the axis of rotation (Ra) of the medial component 74a, the first projection 108 and, thus, the blind bore 114, are eccentric from the axis of rotation (Ra) of the medial component 74a.

The second projection 110 may be received by a blind bore 116 formed into the lateral component 76a. The blind bore 116 may include a female taper that receives a male taper of the second projection 110 when the second projection 110 is inserted into the blind bore 116.

The second projection 110 may include a central axis ($Ca_2$) that is offset from a central axis of the lateral component 76a by a distance ($D_2$). As shown in FIG. 11, when the lateral component 76a is in a neutral state, the central axis of the lateral component 76a is concentric with the axis of rotation (Ra) of the medial component 74a. Accordingly, the distance ($D_2$) is shown relative to the axis of rotation (Ra) of the medial component 74a. Because the second projection 110 and, thus, the blind bore 116, are offset from the central axis of the lateral component 76a, the second projection 110 and the blind bore 116 are eccentric from the central axis of the lateral component 76a.

In operation, a force may be applied to the lateral component 76a to rotate the lateral component 76 about the second projection 110. Because the second projection 110 is offset from the axis of rotation (Ra) of the medial component 74a and from a central axis of the lateral component 76a, rotation of the lateral component 76a about the second projection 110 results in a net offset (i.e., in the plane of FIG. 11) of the lateral component 76 in the direction (Y). As described above with respect to the second condyle 62, such rotation of the lateral component 76a may be performed by the surgeon to properly position the lateral component 76a relative to the head of the proximal radius 94 to allow the engagement surface 90 to properly engage the head of the proximal radius 94.

The surgeon may additionally apply a rotational force to the intermediate component 106, thereby causing the intermediate component 106 to rotate relative to the medial component 74a. Such rotation of the intermediate component 106 relative to the medial component 74a causes the intermediate component 106 to rotate about the first projection 108. Because the first projection 108 is eccentric from the axis of rotation of the medial component 74a, rotation of the intermediate component 106 relative to the medial component 74a results in a net offset (i.e., in the plane of FIG. 11) of the intermediate component 106 in the direction (Z). The net offset of the intermediate component 106 in the direction (Z) likewise causes a net offset (i.e., in the plane of FIG. 11) of the lateral component 76a in the direction (Y), as the lateral component 76a is attached to the first projection 108 of the intermediate component 106 via the second projection 110.

As described, the surgeon may rotate the lateral component 76 about the second projection 110 relative to the intermediate component 106 and may likewise rotate the lateral component 76a along with the intermediate component 106 about the first projection 108 relative to the medial component 74a. While the surgeon may rotate the lateral component 76a relative to the intermediate component 106 and may rotate the intermediate component 106 relative to the medial component 74a, the surgeon could alternatively rotate only the lateral component 76a relative to the intermediate component 106 or could rotate only the intermediate component 106 relative to the medial component 74a. In short, the surgeon could rotate the lateral component 76a relative to the intermediate component 106 and/or may rotate the intermediate component 106 relative to the medial component 74a. Any or all of the foregoing operations may be performed by the surgeon to properly position the engagement surface 90 of the lateral component 76 relative to the head of the proximal radius 94 during surgery.

Once a desired position of the lateral component 76a relative to the intermediate component 106 is achieved, a force may be applied to the lateral component 76 to drive the second projection 110 into the blind bore 116 to allow the male taper of the second projection 110 to fully engage the female taper of the blind bore 116 to fix the lateral component 76 for movement with the intermediate component 106. Likewise, once a desired position of the intermediate component 106 is achieved relative to the medial component 74a, a force may be applied to the intermediate component 106 (via the lateral component 76a) to drive the first projection 108 into the blind bore 114 to allow the male taper of the first projection 108 to fully engage the blind bore 114 of the medial component 74a. As with the lateral component 76a, full engagement of the first projection 108 of the intermediate component 106 and the female taper of the blind bore 114 results in the intermediate component 106 being fixed for movement with the medial component 74a.

Once the lateral component 76a is fixed for movement with the intermediate component 106 and the intermediate component 106 is fixed for movement with the medial component 74a, the lateral component 76a is fixed for movement with the medial component 74a. As a result, the relative position of the engagement surface 90 of the lateral component 76a relative to the head of the proximal radius 94 is likewise fixed. Adjustment of the engagement surface 90 of the lateral component 76 relative to the medial component 74a and the resulting contact of the engagement surface 90 with the head of the proximal radius 94 results in the lateral component 76a adequately supporting the elbow prosthesis 10 relative to the head of the proximal radius 94 while concurrently providing a desired articulation of the lateral component 76a relative to the head of the proximal radius 94.

Figure 12:
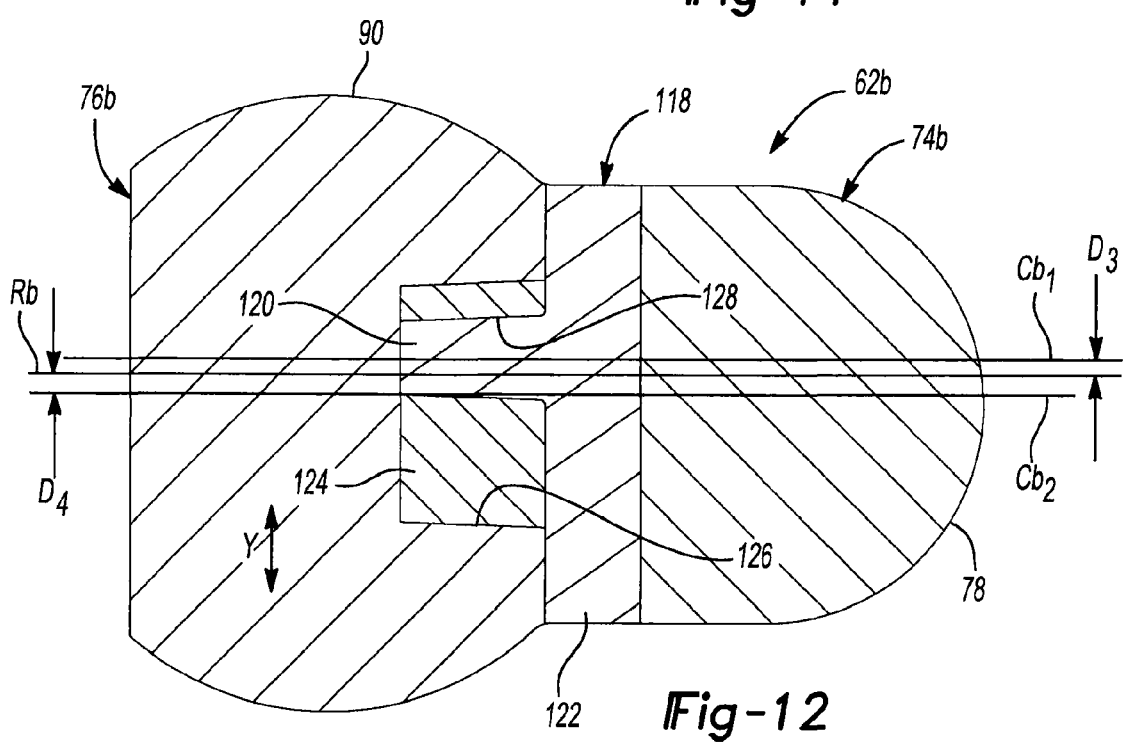
FIG. 12 is a cross-sectional view of an alternate condyle assembly for use in conjunction with the elbow prosthesis of FIG. 1.

With particular reference to FIG. 12, a second condyle 62b is provided for use with the elbow prosthesis 10. The second condyle 62b replaces the second condyle 62 and may include a medial component 74b and a lateral component 76b.

In view of the substantial similarity in structure and function of the components associated with the second condyle 62 with respect to the second condyle 62b, like reference numerals are used hereinafter and in the drawings to identify like components while like reference numerals containing letter extensions are used to identify those components that have been modified.

The lateral component 76b may be attached to the medial component 74b by an intermediate component 118. The intermediate component 118 may include a projection 120 extending from a main body 122. The projection 120 may be received by an insert 124 positioned within a blind bore 126 formed in the lateral component 76b. The projection 120 may include a male taper that is matingly received by a tapered aperture 128 formed in the insert 124.

The projection 120 may be offset from an axis of rotation (Rb) of the medial component 74b. Specifically, a central axis ($Cb_1$) of the projection 120 may be offset from the axis of rotation (Rb) of the medial component 74b by a distance ($D_3$). Accordingly, the projection 120 may be eccentric from the axis of rotation (Rb) of the medial component 74b.

The insert 124 may likewise be offset from the axis of rotation (Rb) of the medial component 74b. Accordingly, a central axis ($Cb_2$) of the insert 124 may be offset from the axis of rotation (Rb) of the medial component 74b by a distance ($D_4$). Accordingly, the insert 124 may be eccentric from the axis of rotation (Rb) of the medial component 74b.

In operation, a surgeon may apply a force to the lateral component 76b to rotate the lateral component and the insert 124 relative to and about the projection 120. Such rotation of the lateral component 76b and the insert 124 relative to and about the projection 120 results in the lateral component 76b moving in the direction (Y) due to the insert 124 being eccentric from the axis of rotation (Rb) of the medial component 74b.

The force applied to the lateral component 76b may also cause rotation of the insert 124 relative to and about the projection 120, which may further result in movement of the lateral component 76b in the direction (Y). As described above with respect to the second condyle 62 and the second condyle 62a, movement of the lateral component 76b in the direction (Y) allows the surgeon to properly position the engagement surface 90 of the lateral component 76b relative to the head of the proximal radius 94.

Once a desired position of the lateral component 76b relative to the head of the proximal radius 94 is achieved, a force may be applied to the lateral component 76b to cause the male taper of the projection 120 to fully engage the tapered aperture 128 of the insert 124 and may cause the male taper of the insert 124 to fully engage the female taper of the blind bore 126 to fix a position of the lateral component 76b relative to the intermediate component 118. Fixing a position of the lateral component 76b relative to the intermediate component 118 likewise fixes a position of the lateral component 76b relative to the medial component 74b and, thus, maintains the adjusted position of the lateral component 76b performed by the surgeon. Accordingly, use of the second condyle 62b in conjunction with the elbow prosthesis 10 ensures that the lateral component 76b supports the elbow prosthesis 10 relative to the head of the proximal radius 94 to provide a desired range of articulation.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An elbow prosthesis comprising:
    a first stem component for attachment to one of a humerus and an ulna;
    a second stem component for attachment to the other of the humerus and the ulna;
    a joint disposed between and coupling said first stem component and said second stem component to permit relative movement between said first stem component and said second stem component about a first axis; and
    a condyle extending from said joint, said condyle rotatably coupled to said joint for rotation about an axis of rotation that is eccentric from said first axis.

2. The elbow prosthesis of claim 1, wherein said condyle includes a first condyle component and a second condyle component.

3. The elbow prosthesis of claim 2, wherein said first condyle component is rotatably attached to said second condyle component.

4. The elbow prosthesis of claim 2, wherein said first condyle component includes an axis of rotation that is eccentric from said first axis and said second condyle component includes an axis of rotation that is substantially concentric with said first axis.

5. The elbow prosthesis of claim 2, wherein one of said first condyle component and said second condyle component includes a projection and the other of said first condyle component and said second condyle component includes a recess operable to rotatably receive said projection.

6. The elbow prosthesis of claim 5, wherein at least one of said projection and said recess includes a taper, said taper permitting relative rotation between said first condyle component and said second condyle component in a first state and restricting relative rotation between said first condyle component and said second condyle component in a second state.

7. The elbow prosthesis of claim 5, wherein said projection and said recess each include an axis of rotation that is offset from said first axis.

8. The elbow prosthesis of claim 5, wherein said projection and said recess each include an axis of rotation that is offset from a central axis of said first condyle component and that is offset from a central axis of said second condyle component.

9. The elbow prosthesis of claim 2, further comprising an intermediate condyle component disposed between said first condyle component and said second condyle component.

10. The elbow prosthesis of claim 9, wherein said intermediate component includes a first projection that is rotatably attached to said first condyle component and is offset from a central axis of said intermediate component and a second projection that is rotatably attached to said second condyle component and is offset from said central axis of said intermediate component.

11. The elbow prosthesis of claim 10, wherein said first projection and said second projection are offset from one another.

12. The elbow prosthesis of claim 1, wherein said axis of rotation is substantially parallel to said first axis.

13. An elbow prosthesis comprising:
    a first stem component for attachment to one of a humerus and an ulna;
    a second stem component for attachment to the other of the humerus and the ulna;
    a joint disposed between and coupling said first stem component and said second stem component to permit relative movement between said first stem component and said second stem component about a first axis; and
    a first condyle component rotatable with one of said first stem component and said second stem component about said first axis; and
    a second condyle component rotatable relative to said first condyle component about a second axis, such that said second condyle component is configured to be coupled to the first condyle component in first and second orientations, the first orientation offset from the second orientation by an angle of rotation about the second axis.

14. The elbow prosthesis of claim 13, wherein said second axis is eccentric from said first axis.

15. The elbow prosthesis of claim 13, wherein said second axis is offset from said first axis.

16. The elbow prosthesis of claim 13, wherein said second axis is different than said first axis.

17. The elbow prosthesis of claim 13, wherein one of said first condyle component and said second condyle component includes a projection and the other of said first condyle component and said second condyle component includes a recess operable to rotatably receive said projection.

18. The elbow prosthesis of claim 17, wherein at least one of said projection and said recess includes a taper, said taper permitting relative rotation between said first condyle component and said second condyle component in a first state and restricting relative rotation between said first condyle component and said second condyle component in a second state.

19. The elbow prosthesis of claim 17, wherein said projection and said recess each include an axis of rotation that is offset from said first axis.

20. The elbow prosthesis of claim 17, wherein said projection and said recess each include an axis of rotation that is offset from a central axis of said first condyle component and that is offset from a central axis of said second condyle component.

21. The elbow prosthesis of claim 13, further comprising an intermediate condyle component disposed between said first condyle component and said second condyle component.

22. The elbow prosthesis of claim 21, wherein said intermediate component includes a first projection that is rotatably attached to said first condyle component and is offset from a central axis of said intermediate component and a second projection that is rotatably attached to said second condyle component and is offset from said central axis of said intermediate component.

23. The elbow prosthesis of claim 22, wherein said first projection and said second projection are offset from one another.

24. The elbow prosthesis of claim 13, wherein said second condyle component is rotatably coupled to said first condyle component for rotation about said second axis.

* * * * *